(12) United States Patent
Clauson et al.

(10) Patent No.: US 8,187,315 B1
(45) Date of Patent: May 29, 2012

(54) PARTIAL STENT FOR TREATMENT OF A VASCULAR ANEURYSM

(75) Inventors: Luke W. Clauson, Redwood City, CA (US); Bryan D. Knodel, Flagstaff, AZ (US); Bernard A. Hausen, Redwood City, CA (US); Scott O. Chamness, Menlo Park, CA (US); Benjamin J. Matthias, San Mateo, CA (US)

(73) Assignee: Cardica, Inc., Redwood City, CA (US)

( * ) Notice: Subject to any disclaimer, the term of this patent is extended or adjusted under 35 U.S.C. 154(b) by 631 days.

(21) Appl. No.: 11/608,435

(22) Filed: Dec. 8, 2006

(51) Int. Cl.
*A61F 2/06* (2006.01)

(52) U.S. Cl. .......................................... 623/1.13; 623/1.1

(58) Field of Classification Search .................. 623/1.1, 623/1.15
See application file for complete search history.

(56) References Cited

U.S. PATENT DOCUMENTS

| 5,192,301 | A | | 3/1993 | Kamiya et al. |
| 5,354,309 | A | | 10/1994 | Schnepp-Pesch et al. |
| 5,637,113 | A | * | 6/1997 | Tartaglia et al. ............. 623/1.42 |
| 5,662,702 | A | | 9/1997 | Keranen |
| 5,741,297 | A | | 4/1998 | Simon |
| 5,766,192 | A | | 6/1998 | Zacca |
| 5,879,366 | A | | 3/1999 | Shaw et al. |
| 5,951,599 | A | | 9/1999 | McCrory |
| 5,954,765 | A | * | 9/1999 | Ruiz ............................ 623/1.15 |
| 6,080,191 | A | | 6/2000 | Summers |
| 6,093,199 | A | | 7/2000 | Brown et al. |
| 6,139,564 | A | | 10/2000 | Teoh |
| 6,149,681 | A | * | 11/2000 | Houser et al. ................ 623/1.12 |
| 6,231,597 | B1 | | 5/2001 | Deem et al. |
| 6,312,446 | B1 | | 11/2001 | Huebsch |
| 6,344,048 | B1 | | 2/2002 | Chin et al. |
| 6,346,117 | B1 | | 2/2002 | Greenhalgh |
| 6,375,668 | B1 | | 4/2002 | Gifford et al. |
| 6,391,037 | B1 | | 5/2002 | Greenhalgh |
| 6,432,128 | B1 | | 8/2002 | Wallace et al. |
| 6,454,780 | B1 | | 9/2002 | Wallace |
| 6,506,204 | B2 | | 1/2003 | Mazzocchi |
| 6,551,303 | B1 | | 4/2003 | Van Tassel et al. |

(Continued)

FOREIGN PATENT DOCUMENTS

EP 1520527 4/2005

(Continued)

OTHER PUBLICATIONS

Pero, Guglielmo, M.D., et. al.; "Treatment of a middle cerebral artery giant aneurysm using a covered stent," J Neurosurg 104:965-968, Jun. 2006.

(Continued)

*Primary Examiner* — David Isabella
*Assistant Examiner* — Joshua Levine
(74) *Attorney, Agent, or Firm* — Brian A. Schar

(57) ABSTRACT

A partial stent may include a backbone and arcuate ribs extending from that backbone; where the ribs have shapes and lengths, and are positioned relative to the backbone, such that when the partial stent is viewed from an end, the ribs collectively define an open arc. A partial stent may include at least one barb extending outward therefrom. The partial stent may be used for treating an aneurysm in a blood vessel, such as a cerebral aneurysm. The partial stent may be placed in the blood vessel adjacent the neck of the aneurysm such that the partial stent substantially covers the neck of the aneurysm.

11 Claims, 3 Drawing Sheets

U.S. PATENT DOCUMENTS

| | | |
|---|---|---|
| 6,585,748 B1 | 7/2003 | Jeffree |
| 6,592,605 B2 | 7/2003 | Lenker et al. |
| 6,648,911 B1 | 11/2003 | Sirhan et al. |
| 6,669,721 B1 | 12/2003 | Bose et al. |
| 6,712,836 B1 | 3/2004 | Berg et al. |
| 6,746,468 B1 | 6/2004 | Sepetka et al. |
| 6,908,479 B2 | 6/2005 | Lau et al. |
| 6,913,618 B2 | 7/2005 | Denardo et al. |
| 6,932,091 B2 | 8/2005 | Frazier et al. |
| 6,942,679 B1 | 9/2005 | Terai |
| 6,949,113 B2 | 9/2005 | Van Tassel et al. |
| 7,122,043 B2 | 10/2006 | Greenhalgh et al. |
| 2002/0173838 A1* | 11/2002 | Frazier .................. 623/1.15 |
| 2003/0171801 A1 | 9/2003 | Bates |
| 2003/0204244 A1 | 10/2003 | Stiger |
| 2004/0034386 A1 | 2/2004 | Fulton et al. |
| 2004/0186556 A1 | 9/2004 | Hogendijk et al. |
| 2005/0033409 A1 | 2/2005 | Burke et al. |
| 2005/0049691 A1 | 3/2005 | Mericle et al. |
| 2005/0125051 A1 | 6/2005 | Eidenschink et al. |
| 2006/0004438 A1 | 1/2006 | Alexander et al. |
| 2006/0015138 A1 | 1/2006 | Gertner |
| 2006/0064151 A1 | 3/2006 | Guterman et al. |
| 2006/0098833 A1 | 5/2006 | Juneau et al. |
| 2006/0155323 A1 | 7/2006 | Porter et al. |
| 2006/0155359 A1 | 7/2006 | Watson |
| 2006/0178694 A1 | 8/2006 | Greenhalgh et al. |
| 2006/0206200 A1 | 9/2006 | Garcia et al. |

FOREIGN PATENT DOCUMENTS

| | | |
|---|---|---|
| EP | 1520530 | 4/2005 |
| EP | 1520531 | 4/2005 |
| WO | WO-00/13593 | 3/2000 |

OTHER PUBLICATIONS

Printout of website page from www.medcompare.com, "JOSTENT(R) Coronary Stent Graft," printed Feb. 2, 2007.

Pero, Gugliemo et al., "Treatment of a middle cerebral artery giant aneurysm using a covered stent", *J Neurosurg 104*, Jun. 2006,965-968.

Vanninen, Ritva et al., "Broad-Based Intracranial Aneurysms Thrombosis Induced by Stent Placement", *Am J. Neuroradiol 24*, (Feb. 2003),263-266.

* cited by examiner

PARTIAL STENT FOR TREATMENT OF A VASCULAR ANEURYSM

FIELD OF THE INVENTION

The invention relates to an apparatus and method for treating a vascular aneurysm.

BACKGROUND

An aneurysm is an abnormal ballooning or dilation of a blood vessel. A cerebral aneurysm is an aneurysm in an artery or vein in the brain. Cerebral aneurysms are more common in adults than in children and more common in women than in men. Cerebral aneurysms commonly arise at the bifurcations of major arteries; most cerebral aneurysms arise on the circle of Willis (where several arteries join near the bottom of the brain) or the middle cerebral artery (MCA) bifurcation.

A common complication of a cerebral aneurysm is rupture, which results in profuse bleeding and causes serious complications including hemorrhagic stroke, permanent nerve damage, hydrocephalus, vasospasm, and/or death. Another complication of a cerebral aneurysm is stroke. Blood pools in the aneurysm, where it becomes isolated from the flow of blood in the brain and subsequently clots. Clots of various sizes can then break off, escape from the cerebral aneurysm into the cerebral vasculature and lodge downstream, causing a stroke.

A variety of options exist for treating cerebral aneurysms. As one example, the aneurysm is clipped from outside before or after it bursts to isolate the aneurysm from the vasculature. However, such clipping requires highly invasive surgical intervention in the brain through the skull. Further, clipping the aneurysm after it bursts does nothing to prevent the potentially-fatal consequences of rupture. It is preferable to treat the aneurysm before it bursts, because patients who receive treatment for an unruptured aneurysm generally require less therapy and recover more quickly. As an example of such treatment, the aneurysm is filled with wire coils. Conventional catheterization techniques are used to insert a catheter into the patient's vasculature at a location outside the brain, such as the groin or the neck, and advance the catheter to the aneurysm using angiography, after which the coils are delivered through the catheter to the aneurysm. The coils fill the aneurysm before it bursts, block it from circulation, and cause the blood to clot. However, the coils may become dislodged from the aneurysm and enter the vasculature, causing stroke in the same manner as blood clots that become dislodged from the aneurysm. Further, smaller clots may still break off and escape from the cerebral aneurysm, resulting in stroke.

DETAILED DESCRIPTION

Figure 1:
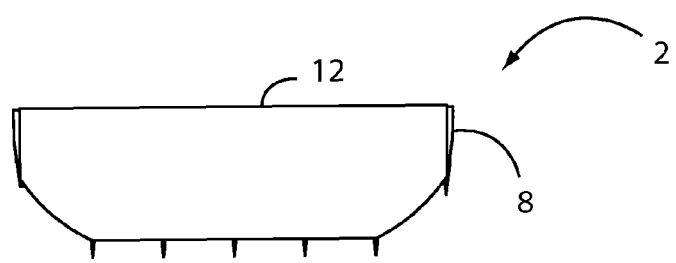
FIG. 1 is a side view of a partial stent that includes a cover.
Figure 2:
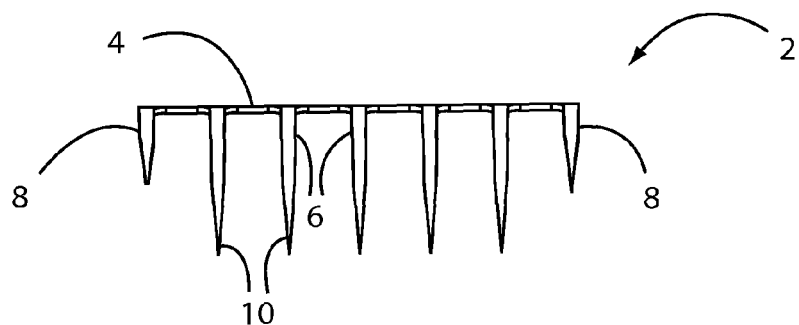
FIG. 2 is a side view of the partial stent of FIG. 1 with the cover removed for clarity.

Referring to FIGS. 1-6, a partial stent 2 is shown. Referring in particular to FIG. 2, the term "partial stent" refers to a stent that, unlike a conventional coronary stent, does not describe a complete circumference when viewed on end. Instead, when viewed on end, the partial stent 2 is generally arc-shaped. The partial stent 2 is sized and shaped to allow delivery via a standard catheter, as described in greater detail below. Alternately, the partial stent 2 may be sized and/or shaped differently.

Figure 4:
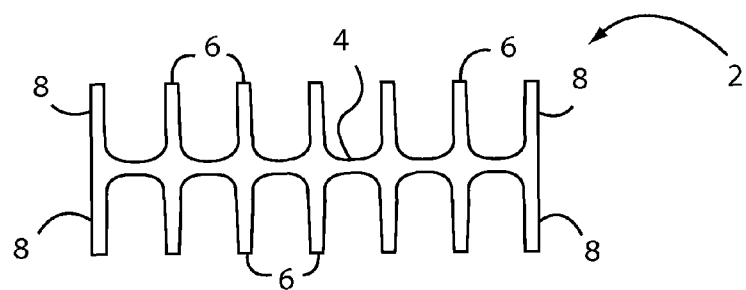
FIG. 4 is a top view of the partial stent of FIG. 1 with the cover removed for clarity.
Figure 5:
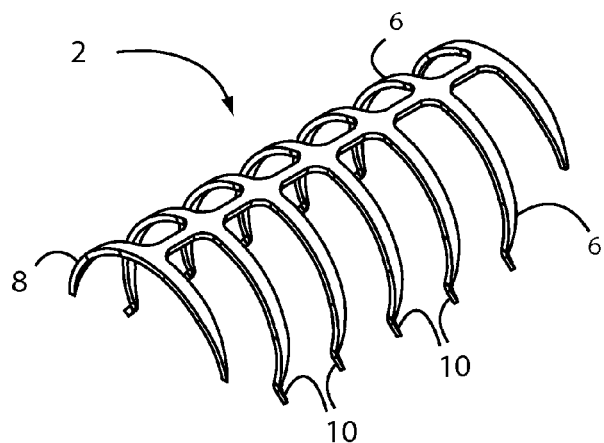
FIG. 5 is a perspective view of the partial stent of FIG. 1 with the cover removed for clarity.

Referring to FIG. 4, the partial stent 2 includes a backbone 4. The backbone 4 may be shaped in any suitable manner. As one example, the backbone 4 is generally linear, with a length substantially larger than its width or thickness. The backbone 4 may be generally parallel to the longitudinal centerline of the partial stent 2. As another example, the backbone 4 may be curved along a tortuous or non-tortuous path. The backbone 4 is flexible, at least in part, to allow delivery of the partial stent 2 to a treatment site via catheter. As one example, the entire backbone 4 may be flexible, as a consequence of the material from which the backbone 4 is fabricated, as well as the thickness and shape of the backbone 4. As another example, the backbone 4 may include substantially rigid segments connected by substantially flexible segments, such that the backbone 4 overall is flexible. As another example, the partial stent 2 may be small enough that the backbone 4 may be rigid.

Referring to FIGS. 1-6, one or more long ribs 6 may extend from the backbone 4. The long ribs 6 may be substantially as wide as the backbone 4. Alternately, at least one of the long ribs 6 may be wider or narrower than the backbone 4. The long ribs 6 extend substantially perpendicularly from the backbone 4. Alternately, at least one of the long ribs 6 extends from the backbone 4 at an angle other than perpendicular. Each long rib 6 is curved about a radius of curvature similar to or larger than the expected radius of curvature of a patient's blood vessel at the treatment site. One or more long ribs 6 may be curved in one or more additional directions as well.

Two or more ribs 6 may be paired along the backbone 4. That is, two long ribs 6 both may extend from a location at a first distance from an end of the backbone 4, each long rib 6 extending laterally from a different side of the backbone 4, where those two long ribs 6 collectively form a pair. Each pair of long ribs 6 may collectively have a generally C-shaped appearance as viewed from an end of the partial stent 2. Alternately, at least one pair of long ribs 6 may collectively form a different shape. Pairs of long ribs 6 may be substantially evenly spaced along the backbone 4. Alternately, at least some of the pairs of long ribs 6 may be spaced differently along the backbone 4. Alternately, at least two of the long ribs 6 are not paired, and instead are offset from one another. The term "offset" refers to the positioning of one long rib 6 at a first distance from an end of the backbone 4 without a corresponding long rib 6 being positioned at that first distance from the end of the backbone 4, and the positioning of another long rib 6 at a second distance from an end of the backbone 4 without a corresponding long rib 6 being positioned at that second distance from the end of the backbone 4. Thus, ribs that are paired are not offset, and ribs that are offset are not paired. By offsetting two or more long ribs 6 along the backbone 4, the long ribs 6 may be compressed inward to a greater extent than if those long ribs 6 were not offset, thereby allowing the partial stent 2 to be inserted through a catheter having a smaller lumen.

Each long rib 6 extends along an arc that may have any suitable length, but which does not describe a complete circle or other closed geometric shape. That is, no long rib 6 is circular, oval-shaped, or shaped in any other closed manner. Further, referring in particular to FIG. 3, the long ribs 6 have arc shapes and lengths, and are positioned in a manner relative to the backbone 4, such that when the partial stent 2 is viewed from either end, the long ribs 6 collectively define an arc that may have any suitable length, but which does not form a complete circle or other closed geometric shape.

Referring to FIGS. 2-3 and 5-6, each long rib 6 may include a barb 10 at its end, where the barb 10 extends in a direction outward relative to the long rib 6. Each barb 10 has a length less than the expected thickness of the vascular tissue in which the partial stent 2 is to be utilized. In this way, the barbs 10 assist in holding the partial stent 2 in place at the treatment site, without penetrating completely through a wall of the blood vessel in which the partial stent 2 is placed. Each barb 10 may extend outward a distance substantially the same as the thickness of the corresponding long rib 6, as long as that distance is less than the expected thickness of the vascular tissue in which the partial stent 2 is to be utilized. Alternately, each barb 10 may extend a greater or lesser distance from the corresponding long rib 6. At least one barb 10 may have a tapered or pointed end to facilitate penetration of tissue. However, at least one barb 10 may have a cross-section small enough to penetrate tissue readily without being tapered or pointed. Each barb 10 may be straight or curved. The barbs 10 may all have the same length and/or shape. Alternately, at least one barb 10 has a length and/or shape different from at least one other barb 10. Alternately, one or more long ribs 6 include two or more barbs 10. Alternately, one or more long ribs 6 include at least one barb 10 positioned at a location other than at the end of the long rib 6. Alternately, the barbs 10 may be omitted from the partial stent 2 altogether.

Referring to FIGS. 1-6, one or more short ribs 8 optionally may extend from the backbone 4 in addition to the one or more long ribs 6 extending from the backbone 4. The short ribs 8 may be shaped similarly to the long ribs 6, but are shorter in length than the long ribs 6. The short ribs 8 may be substantially as wide as the backbone 4. Alternately, at least one of the short ribs 8 may be wider or narrower than the backbone 4. The short ribs 8 extend substantially perpendicularly from the backbone 4. Alternately, at least one of the short ribs 8 extends from the backbone 4 at an angle other than perpendicular. Each short rib 8 is curved about a radius of curvature similar to or larger than the expected radius of curvature of a patient's blood vessel at the treatment site. One or more short ribs 8 may be curved in one or more additional directions as well. Advantageously, one or more of the short ribs 8 are positioned at or in proximity to an end of the backbone 4. Placement of the short ribs 8 at one or both ends of the partial stent 2 may enhance the flexibility of the partial stent 2 and/or may allow smoother flow of blood over the partial stent 2 after it has been placed at a treatment site. Alternately, the long ribs 6 or the short ribs 8 are not used, such that all of the ribs extending from the backbone 4 are substantially the same length. Alternately, ribs of one or more different lengths than the ribs 6, 8 may be used. As one example, each rib may have a different length than one or more other ribs.

The short ribs 8 may be paired along the backbone 4 in the same manner that the long ribs 6 may be paired. Each pair of short ribs 8 may collectively have a generally C-shaped appearance as viewed from an end of the partial stent 2. Alternately, at least one pair of short ribs 8 may collectively form a different shape. The pairs of short ribs 8 may be placed at or in proximity to the ends of the backbone 4. Alternately, at least one of the pairs of short ribs 8 may be connected to a different location on backbone 4. Alternately, at least two of the short ribs 8 are not paired, and instead are offset from one another in the same manner that at least two of the long ribs 6 may be offset from one another.

Each short rib 8 extends along an arc that may have any suitable length, but which does not describe a complete circle or other closed geometric shape. That is, no short rib 8 is circular, oval-shaped, or shaped in any other closed manner. Further, referring in particular to FIG. 3, the short ribs 8 have arc shapes and lengths, and are positioned in a manner relative to the backbone 4, such that when the partial stent 2 is viewed from either end, the ribs 6, 8 collectively define an arc that may have any suitable length, but which does not describe a complete circle or other closed geometric shape. In this way, the partial stent 2 describes an incomplete circumference, which also may be characterized as an open arc, when viewed from either end thereof. This property of the partial stent 2 allows the partial stent to be placed at a bifurcation in the blood vessel without impeding flow therethrough, as described in greater detail below.

Referring to FIGS. 2-3 and 5-6, each short rib 8 may include a barb 10 at its end, where the barb 10 extends in a direction angled outward relative to the short rib 8. Each barb 10 has a length less than the expected thickness of the vascular tissue in which the partial stent 2 is to be utilized. Each barb 10 may extend outward a distance substantially the same as the thickness of the corresponding short rib 8, as long as that distance is less than the expected thickness of the vascular tissue in which the partial stent 2 is to be utilized. Alternately, each barb 10 may extend a greater or lesser distance from the corresponding short rib 8. At least one barb 10 may have a tapered or pointed end to facilitate penetration of tissue. However, at least one barb 10 may have a cross-section small enough to penetrate tissue readily without being tapered or pointed. Each barb 10 may be straight or curved. The barbs 10 may all have the same length and/or shape. Alternately, at least one barb 10 has a length and/or shape different from at least one other barb 10. Alternately, one or more short ribs 8 include two or more barbs 10. Alternately, one or more short ribs 8 include at least one barb 10 positioned at a location other than at the end of the short rib 8. Alternately, the barbs 10 may be omitted from the partial stent 2 altogether.

Figure 3:
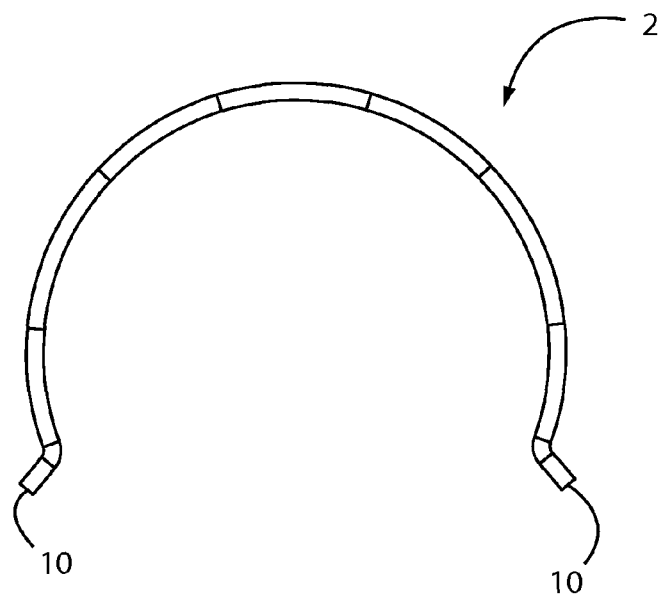
FIG. 3 is an end view of the partial stent of FIG. 1.

Referring to FIGS. 2-4, the backbone 4 and ribs 6, 8 may be referred to collectively as the body of the partial stent 2. The backbone 4 and ribs 6, 8 may be fabricated from a superelastic material such as nickel-titanium alloy, from an elastic material, or from a plastically-deformable material such as stainless steel. Advantageously, the backbone 4 and ribs 6, 8 of the partial stent are superelastic and metallic. The body of the partial stent 2 may be fabricated from a single piece of raw material, such as a tube of nickel-titanium alloy. If so, the body of the partial stent 2 may be fabricated by laser-cutting, machining or otherwise manipulating that tube. Alternately, the backbone 4 and/or one or more of the ribs 6, 8 may be fabricated separately from one another and later connected together.

Figure 6:
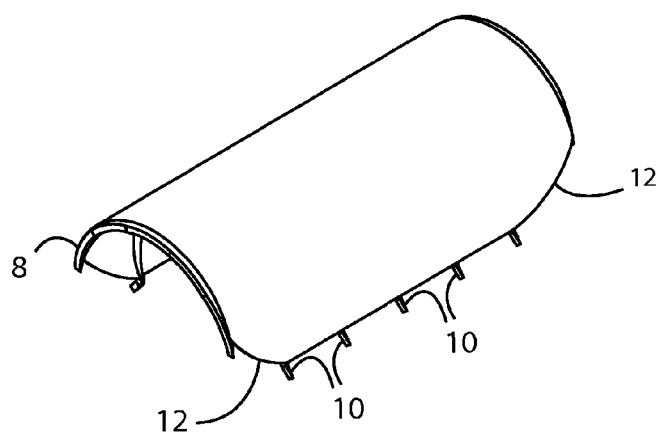
FIG. 6 is a perspective view of the partial stent of FIG. 1.
Figure 7:
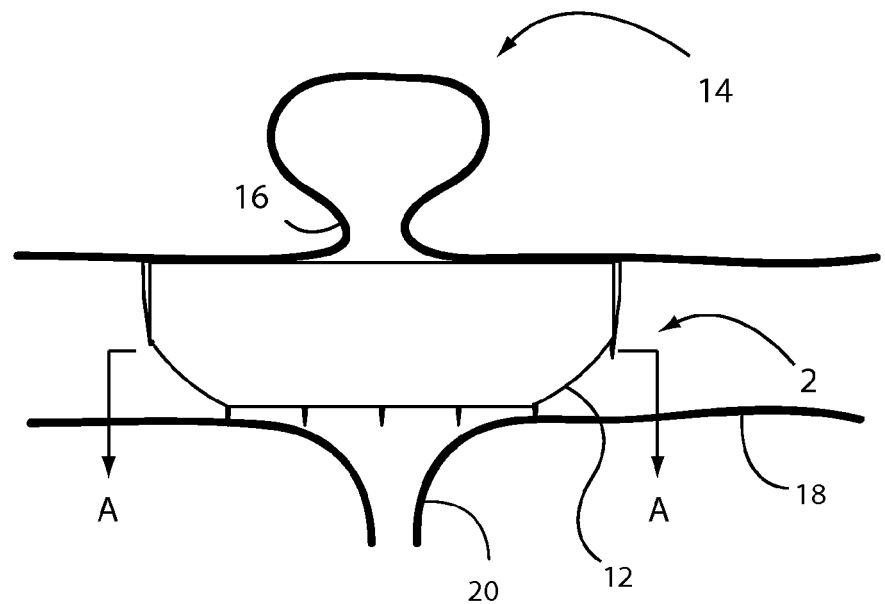
FIG. 7 is a cutaway view of the partial stent after placement at an exemplary location on in a patient's vasculature.

Referring to FIGS. 1 and 6, the partial stent 2 may include a cover 12. The cover 12 may have any suitable thickness. Advantageously, the cover 12 is a thin shell or membrane that is thinner than the backbone 4 of the partial stent 2. The cover 12 is located on the outer surface of the body of the partial stent 2. The cover 12 covers at least part of the body of the partial stent 2. As one example, the cover 12 is shaped in a manner that covers the backbone 4 of the partial stent and the ribs 6, 8, with the exception of the barbs 10. As shown in FIG. 6, one example of the cover 12 may be characterized as being unitary and generally saddle-shaped. However, the cover 12 may have any other suitable shape. The cover 12 covers the neck of an aneurysm at a treatment site to isolate that aneurysm from the vasculature, as described in greater detail below. The cover 12 may be rigid, flexible, or rigid in part and flexible in part.

The cover 12 may be fabricated from any suitable material, such as but not limited to polytetrafluoroethylene (PTFE), polymer, DACRON® brand polyester, a combination of one or more of those materials, or one or more different or additional materials. Advantageously, the cover 12 is composed of PTFE. The cover 12 may be connected to the body of the partial stent 2 in any suitable manner, such as by crimping, adhesive, one or more connectors, the use of molding or overmolding, or any other or additional structures, mechanisms or methods. Alternately, the cover 12 may be fabricated integrally with the body of the partial stent 2. That is, the cover 12 may be fabricated from the same piece of raw material as the remainder of the partial stent 2. Advantageously, the cover 12 is connected to the body of the partial stent 2 in a manner that minimizes or eliminates motion or "flapping" of the cover 12 after the partial stent 2 has been placed at a treatment site in the vasculature. For example, where the cover 12 is fabricated from a thin membrane, the cover 12 is stretched tautly and smoothly over the body of the partial stent 2. The cover 12 is compliant enough to generally conform to the vasculature and substantially slow or stop flow into the aneurysm.

Alternately, the cover 12 has multiple independent and discrete components. For example, the cover 12 may include a number of individual elements, each positioned between adjacent ribs 6, 8 and next to the backbone. In that way, the cover 12 need not add thickness to the partial stent 2. As another example, the cover 12 may include two or more sheets placed next to one another, or overlapping, on the outer surface of the partial stent 2. Alternately, multiple independent and discrete components of the cover 12 may be positioned relative to the body of the partial stent 2 and one another in any other suitable manner. Alternately, the cover 12 is not used, in which case the partial stent 2 may be configured differently in order to cover the neck of the aneurysm at the treatment site. For example, if the partial stent does not include the cover 12, the backbone 4 may be wider in order to cover the neck of the aneurysm at the treatment site.

One or more components of the partial stent 2, or the partial stent 2 in its entirety, may contain or be treated with one or more pharmaceutical compounds. As one example, at least part of the partial stent 2 may contain or be treated with one or more antiproliferative pharmaceutical compounds to prevent or reduce the likelihood of stenosis at the treatment site.

Operation

In this section of the document, treatment of a cerebral aneurysm is described. However, the partial stent 2 is not limited to use in treating a cerebral aneurysm; any other suitable aneurysm in the vasculature may be treated with the partial stent 2. Because this procedure is interventional and not surgical, it can be performed in a catheterization laboratory rather than an operating room. A guidewire is introduced into the patient's vasculature in a standard manner. Access to the vasculature may be through the femoral artery, carotid artery, or any other suitable blood vessel. Using standard fluoroscopic visualization or other suitable navigation techniques, the distal end of the guidewire is advanced through the vasculature to a location in proximity to the treatment site, which is the neck of the aneurysm. Alternately, the distal end of the catheter may be advanced to the treatment site without the use of a guidewire.

The catheter may be a standard balloon catheter, having a balloon at or near its distal end. If so, the partial stent 2 may be placed over the balloon prior to advancement of the catheter to the treatment site. The partial stent 2 may be detachably connected to the balloon or other portion of the catheter, such that the partial stent 2 is pre-placed on the balloon and the user need not load the partial stent 2 onto the balloon. The balloon catheter is advanced to a location at which the partial stent 2 is positioned at the neck of the aneurysm and oriented such that the cover 12 is positioned substantially over the neck 16 of the aneurysm 14. The cover 12 or other portion of the partial stent 2 may include one or more markers visible under fluoroscopy or other imaging to allow the user to orient the cover 12 over the neck 16 of the aneurysm 14. The partial stent 2 first may be advanced into the blood vessel 18 to a location adjacent to the neck 16 of the aneurysm 14, then oriented such that the cover 12 is next to the neck 16 of the aneurysm. Alternately, the partial stent 2 may be advanced to the neck 16 of the aneurysm 14 in such a manner that it arrives at the neck 16 of the aneurysm 14 already in the proper orientation.

Figure 8:
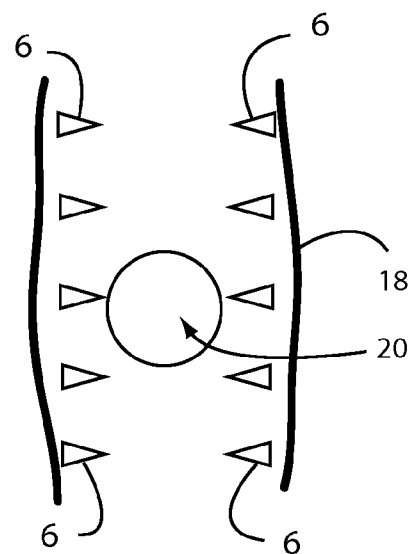
FIG. 8 is a cross-section view of the partial stent along line A-A of FIG. 7 after placement in a patient's vasculature.

The partial stent 2 is movable between two states: a low-profile state and an expanded state. In the low-profile state, the partial stent 2 has a smaller profile when viewed on end than in the expanded state. In this way, the partial stent 2 can be navigated more easily through the vasculature to the treatment site. Referring to FIG. 8, the treatment site is in a blood vessel 18, and may be at the junction or bifurcation between that blood vessel 18 and a second blood vessel 20. Advantageously, the partial stent 2 is initially in the low-profile state on the balloon. After the partial stent 2 has been advanced to the treatment site, the balloon is inflated in a standard manner, such as by forcing saline solution into the balloon. Inflation of the balloon causes the partial stent 2 to expand outward to its expanded state in the blood vessel 18. Such expansion may be radial, longitudinal, or both. Where the body of the partial stent 2 is plastically deformable, such as where the body is composed of stainless steel, inflation of the balloon causes the ribs 6, 8 to plastically deform outward to the expanded state. The backbone 4 may or may not expand. The ribs 6, 8 plastically deform outward to a degree that is directly related to the diameter of the balloon and the degree to which the balloon is inflated. Where the body of the partial stent 2 is superelastically deformable, inflation of the balloon causes the ribs 6, 8 to transition from their first bistable state to their second, expanded bistable state. The backbone 4 may or may not expand. The ribs 6, 8 seat against the wall of the blood vessel 18 as they deform outward; expansion of the balloon applies radial force to the ribs 6, 8 and seats them against the wall of the blood vessel 18. Further, as the ribs 6, 8 deform outward, the barbs 10 are pushed into the wall of the blood vessel 18. The barbs 10 are shorter than the wall thickness of the blood vessel 18, such that they do not penetrate completely through the wall. Instead, penetration of the barbs 10 into the wall assists in anchoring the partial stent 2 at the treatment site and holding the partial stent 2 in place.

The cover 12 now substantially covers the neck 16 of the aneurysm 14, substantially isolating the aneurysm 14 from the vasculature. The cover 12 is compliant enough to generally conform to the wall of the blood vessel 18 and substantially slow or stop flow into the aneurysm 14. Referring to FIG. 8, where the neck 16 of the aneurysm 14 is located substantially across from the junction between a second vessel 20 and the blood vessel 18, the partial circumference of the partial stent 2 allows blood to flow unimpeded from the second vessel 20 into the blood vessel 18. That is, because the ribs 6, 8 are arcuate but do not extend all the way around the circumference of the blood vessel 18, the ribs 6, 8 do not extend into or across the junction between the vessels 18, 20. In this way, the partial stent 2 can be placed at a bifurcation between blood vessels without impeding blood flow therethrough, reducing the likelihood of clot formation on the partial stent 2. The catheter and guidewire are then withdrawn from the treatment site and removed from the patient, and the procedure is complete.

Alternately, the partial stent 2 may be advanced to the treatment site through the lumen of the catheter. Alternately, the catheter is not used. If not, the partial stent 2 may be detachably connected to the guidewire, advantageously at or near the distal end of the guidewire. The guidewire is manipulated until the partial stent 2 is positioned at the neck of the aneurysm and oriented such that the cover 12 is positioned substantially over the neck 16 of the aneurysm 14. The cover 12 or other portion of the partial stent 2 may include one or more markers visible under fluoroscopy or other imaging to allow the user to orient the cover 12 over the neck 16 of the aneurysm 14. The partial stent 2 first may be advanced into the blood vessel 18 to a location adjacent to the neck 16 of the aneurysm 14, then oriented such that the cover 12 is next to the neck 16 of the aneurysm. Alternately, the partial stent 2 may be advanced to the neck 16 of the aneurysm 14 in such a manner that it arrives at the neck 16 of the aneurysm 14 already in the proper orientation.

Where the catheter is not used, the body of the partial stent 2 is advantageously elastic or superelastic, biased to its expanded state, and detachably connected to the guidewire in such a manner that the partial stent 2 self-expands to the expanded state after it is released. The partial stent 2 is advanced to the treatment site. After the partial stent 2 has been positioned longitudinally at the treatment site and oriented correctly, the partial stent 2 may be released from the guidewire in any suitable manner. As a result, the partial stent 2 self-expands outward to its expanded state. The ribs 6, 8 seat against the wall of the blood vessel as they deform outward. Further, as the ribs 6, 8 deform outward, the barbs 10 are pushed into the wall of the blood vessel. The barbs 10 are shorter than the wall thickness of the blood vessel, such that they do not penetrate completely through the wall. Instead, penetration of the barbs 10 into the wall assists in anchoring the partial stent in place at the treatment site. The cover 12 now covers the neck 16 of the aneurysm 14, isolating the aneurysm 14 from the vasculature. The catheter and guidewire are then withdrawn from the treatment site and removed from the patient, and the procedure is complete.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Further, the invention is not limited to use with cerebral aneurysms, and may be used to treat other conditions in the brain or in other parts of the body. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A partial stent, comprising:
   a backbone;
   a plurality of arcuate ribs extending from said backbone; wherein said ribs are shaped and sized, and positioned relative to said backbone, such that said ribs collectively define a generally C-shaped open arc when the partial stent is viewed on end, and such that the free ends of the ribs collectively define an opening; and
   a cover connected to said backbone, wherein substantially all of said cover is positioned outside of said backbone; wherein said ribs are movable from a first state to a second, expanded state, and wherein both in said first state and said second state each said rib has one said free end.

2. The partial stent of claim 1, wherein said cover is a membrane.

3. The partial stent of claim 1, wherein at least one said rib is shorter than at least one other said rib.

4. The partial stent of claim 1, wherein at least two said ribs are paired along said backbone.

5. The partial stent of claim 4, wherein said paired ribs are substantially evenly spaced along said backbone.

6. The partial stent of claim 1, wherein at least two said ribs are offset.

7. The partial stent of claim 1, wherein said backbone is substantially linear.

8. The partial stent of claim 1, further comprising at least one barb extending outward from at least one said rib.

9. The partial stent of claim 8, wherein at least one said barb extends from the distal end of a corresponding said rib.

10. The partial stent of claim 1, wherein said backbone is wider than said ribs.

11. The partial stent of claim 1, wherein said ribs are composed of superelastic material.

* * * * *